US011099057B2

(12) United States Patent
Madadin

(10) Patent No.: US 11,099,057 B2
(45) Date of Patent: Aug. 24, 2021

(54) GROSSING WORKSTATION WITH ELECTRONIC SCALE

(71) Applicant: Imam Abdulrahman Bin Faisal University, Dammam (SA)

(72) Inventor: Mohammed Saleh Madadin, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 15/606,533

(22) Filed: May 26, 2017

(65) Prior Publication Data

US 2018/0055706 A1 Mar. 1, 2018

(51) Int. Cl.
*G01G 21/22* (2006.01)
*H04N 5/225* (2006.01)
*G01G 19/52* (2006.01)
*A61B 16/00* (2006.01)
*G01G 21/28* (2006.01)
*G06T 7/62* (2017.01)

(52) U.S. Cl.
CPC .............. *G01G 21/22* (2013.01); *A61B 16/00* (2013.01); *G01G 19/52* (2013.01); *G01G 21/28* (2013.01); *G06T 7/62* (2017.01); *H04N 5/2251* (2013.01); *H04N 5/2256* (2013.01); *G06T 2207/10028* (2013.01); *G06T 2207/30004* (2013.01)

(58) Field of Classification Search
CPC ......... G01G 19/52; G01G 21/22; A61B 16/00
See application file for complete search history.

(56) References Cited

U.S. PATENT DOCUMENTS 4,659,172 A * 4/1987 Cavan ............... G06K 9/74
356/237.5
6,434,329 B1 * 8/2002 Dube ............... F16M 11/126
128/897

(Continued)

FOREIGN PATENT DOCUMENTS

| CN | 202277014 U | * | 6/2012 |
| CN | 204142141 U | | 2/2015 |
| CN | 205120401 U | | 3/2016 |

OTHER PUBLICATIONS

Spot Imaging, Pathstand Grossing Station Product Specification, available at http://www.spotimaging.com/downloads/public/pdf/pathstand.pdf; Product demonstrated at https://www.youtube.com/watch?v=eLPts3lS2K4 on Jan. 6, 2016 (Year: 2016).*

(Continued)

*Primary Examiner* — Jayanti K Patel
*Assistant Examiner* — Christopher Kingsbury Glover
(74) *Attorney, Agent, or Firm* — Oblon, McClelland, Maier & Neustadt, L.L.P.

(57) ABSTRACT

A grossing workstation comprising an electronic scale, screen, and camera holder is described. The camera holder may be mounted on a flexible or articulating arm in order to attach a digital camera for specimen imaging. A computing device in the scale may store digital copies of specimen images or measurements. The computing device may furthermore control movements of the balance pan and camera holder in order to automatically image a specimen at different view angles.

12 Claims, 6 Drawing Sheets

(56) References Cited

U.S. PATENT DOCUMENTS

| | | | | |
|---|---|---|---|---|
| 6,771,493 | B2* | 8/2004 | Chen | G06F 1/1616 |
| | | | | 292/95 |
| 9,547,898 | B2 | 1/2017 | Hall et al. | |
| 2005/0288571 | A1* | 12/2005 | Perkins | A61B 5/0002 |
| | | | | 600/407 |
| 2008/0056569 | A1* | 3/2008 | Williams | G06T 5/50 |
| | | | | 382/173 |
| 2011/0067781 | A1* | 3/2011 | Osborne | B65B 3/003 |
| | | | | 141/37 |
| 2014/0018658 | A1* | 1/2014 | Karo | A61B 5/0537 |
| | | | | 600/390 |
| 2014/0275842 | A1* | 9/2014 | Curry | A61B 5/6892 |
| | | | | 600/301 |
| 2015/0279032 | A1* | 10/2015 | Hall | G06T 11/203 |
| | | | | 382/128 |
| 2016/0231167 | A1* | 8/2016 | Masin | G06K 7/10386 |
| 2018/0000467 | A1* | 1/2018 | Hynna | A61B 34/20 |
| 2018/0042528 | A1* | 2/2018 | Helwa | A61B 5/6833 |

OTHER PUBLICATIONS

Scientek Hospital and Laboratory Equipment, "Pathology Workstations", URL: http://scientek.net/wp-content/uploads/2016/01/Pathology-Workstations.pdf, 8 Pages total, (2016).

Leong, A.S.Y., et al., "An Advanced Digital Image-Capture Computer System for Gross Specimens: A Substitute for Gross Description", Pathology, vol. 32, pp. 131-135, (2000).

* cited by examiner

GROSSING WORKSTATION WITH ELECTRONIC SCALE

CROSS-REFERENCE TO RELATED APPLICATIONS

The present application claims the benefit of priority to The Kingdom of Saudi Arabia Patent App. No. 116370918, filed on Sep. 1, 2016, the entire content and disclosure of which is incorporated herein by reference.

BACKGROUND OF THE INVENTION

Technical Field

The present invention relates to a grossing workstation for pathology and autopsy.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Forensic autopsy is an important part of a death investigation. Forensic autopsy involves dissecting a dead body to determine the cause of death, and pathological samples such as different organs may be further documented as evidence. A forensic autopsy may be conducted by a forensic pathologist.

During an autopsy procedure, this pathologist needs to examine, weigh, measure, and photograph the body organs to document an injury or disease. Over the course of a complete investigation, these tasks can add up to a significant amount of time, given that the pathologist must enter data, update case files, adjust a camera, and measure a specimen, all while frequently removing and replacing gloves to prevent contamination.

In view of the foregoing, one objective of the present invention is to provide a grossing workstation with an electronic scale, a camera holder, and automatic measurement and record-keeping abilities.

BRIEF SUMMARY OF THE INVENTION

According to a first aspect, the present disclosure relates to a grossing workstation, comprising an electronic scale having a housing with a top side, a computing device disposed within the housing and electrically connected to a load cell, a balance pan located on the top side of the housing, the balance pan being in contact with the load cell, a screen attached to the housing and electrically connected to the computing device, and a camera holder attached to the housing by an arm, and electrically connected to the computing device. The camera holder is configured to secure and electrically connect with a digital camera to image a specimen on the balance pan.

In one embodiment, the grossing workstation further comprises at least one input device electrically connected to the computing device.

In a further embodiment, the at least one input device is a microphone, a barcode scanner, an infrared camera, and/or an RFID tag reader.

In a further embodiment, the at least one input device is a keyboard, a touchscreen, or a button panel, and is slidably attached to one or more rails and configured to slide between a first position within an interior of the housing and a second position extending from a first side of the housing.

In one embodiment, the screen is attached to a second side of the housing opposing the first side.

In a further embodiment, the screen is attached to the second side of the housing by a hinge or an adjustable mount.

In one embodiment, the arm is flexible or articulating.

In one embodiment, the camera holder, the arm, or both comprises a motor and an actuator. The motor is configured to receive an electrical signal from the computing device and move the camera holder via the actuator.

In a further embodiment, where the camera holder, the arm, or both comprises a motor and an actuator, the actuator is a lead screw, a belt drive, a worm drive, a rack and pinion drive, and/or a chain drive.

In a further embodiment, where the camera holder, the arm, or both comprises a motor and an actuator, the arm is connected to the housing at both ends to form an arch.

In one embodiment, the balance pan has one or more graduated markings configured to measure one or more dimensions of a specimen.

In one embodiment, the balance pan comprises at least one sensor electrically connected to the computing device and configured to measure a physical property of a specimen.

In a further embodiment, the sensor is an ultrasonic transducer, a spectrometer, a thermometer, and/or an electrode.

In one embodiment, the balance pan comprises a pedestal extending from a central region of a bottom side of the balance pan. The pedestal traverses the housing and contacts the load cell, and the balance pan is configured to be rotatable.

In a further embodiment, the grossing workstation also has a pedestal motor electrically connected to the computing device and configured to rotate the pedestal.

In one embodiment, the balance pan comprises a rack, which is configured to elevate a specimen.

In one embodiment, the grossing workstation has a second arm attached to the housing. This second arm has one or more lights configured to illuminate a specimen.

According to a second aspect, the present disclosure relates to a method of measuring a specimen with the grossing workstation of the first aspect. The method involves placing a specimen on the balance pan, pushing a button on the camera holder, housing, or screen to trigger the computing device to receive a first image from a digital camera secured to the camera holder, and storing the first image with a weight measurement of the specimen.

In one embodiment, the method further comprises the step of rotating the specimen or moving the camera holder, capturing at least one second image of the specimen with the digital camera, and receiving and storing the at least one second image with the computing device.

In a further embodiment, the method further comprises the step of calculating a bulk density of the specimen from the first image, the at least one second image, and the weight measurement.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
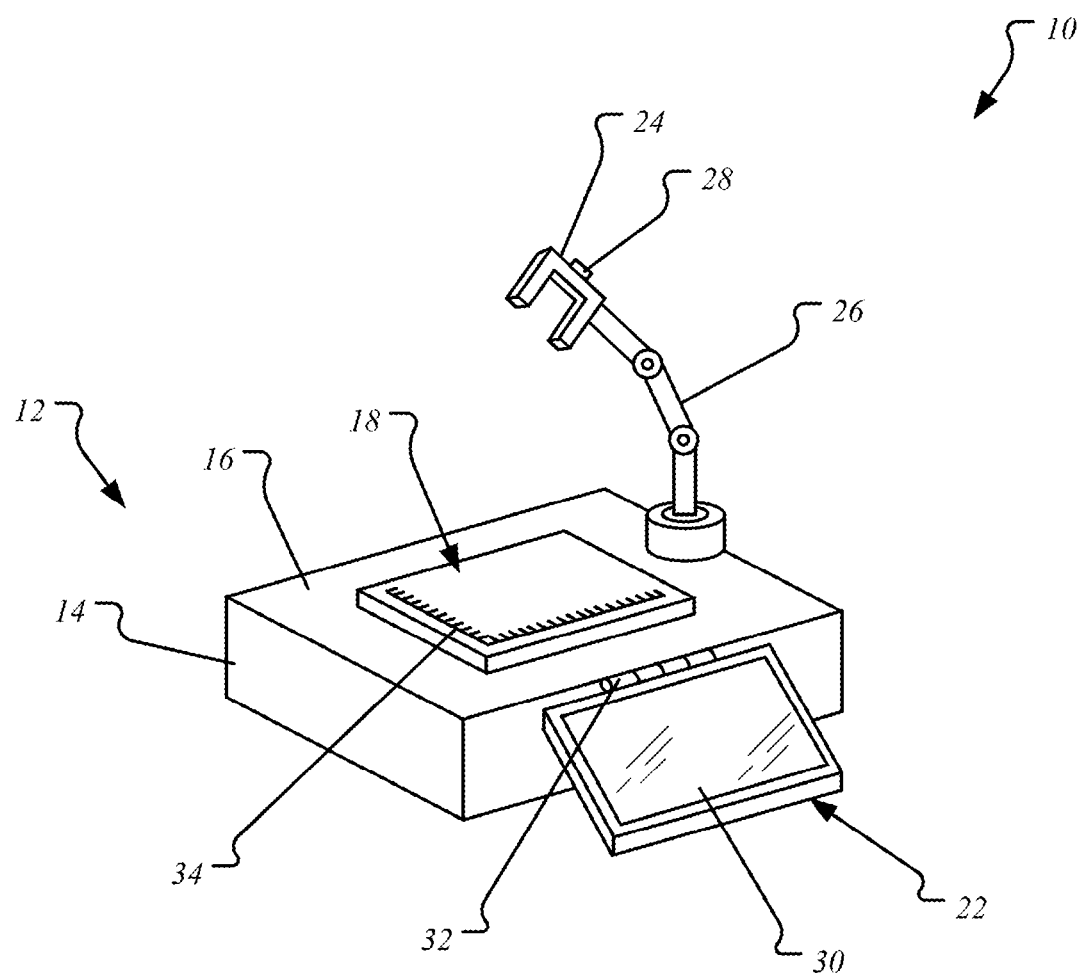
FIG. 1 shows a perspective view of a grossing workstation with a camera holder on an articulating arm and a screen attached by an adjustable hinge.

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more." Within the description of this disclosure, where a numerical limit or range is stated, the endpoints are included unless stated otherwise. Also, all values and subranges within a numerical limit or range are specifically included as if explicitly written out.

According to a first aspect, the present disclosure relates to a grossing workstation 10, comprising an electronic scale 12 having a housing 14 with a top side 16, a computing device 80 disposed within the housing 14 and electrically connected to a load cell 20, a balance pan 18 located on the top side 16 of the housing 14, the balance pan 18 being in contact with the load cell 20, a screen 22 attached to the housing 14 and electrically connected to the computing device 80, and a camera holder 24 attached to the housing 14 by an arm 26, and electrically connected to the computing device 80. The camera holder 24 is configured to secure and electrically connect with a digital camera to image a specimen 84 on the balance pan 18. As used herein, "workstation" refers to the grossing workstation 10 of the first aspect, and may also be called a "gross pathology station."

Figure 2:
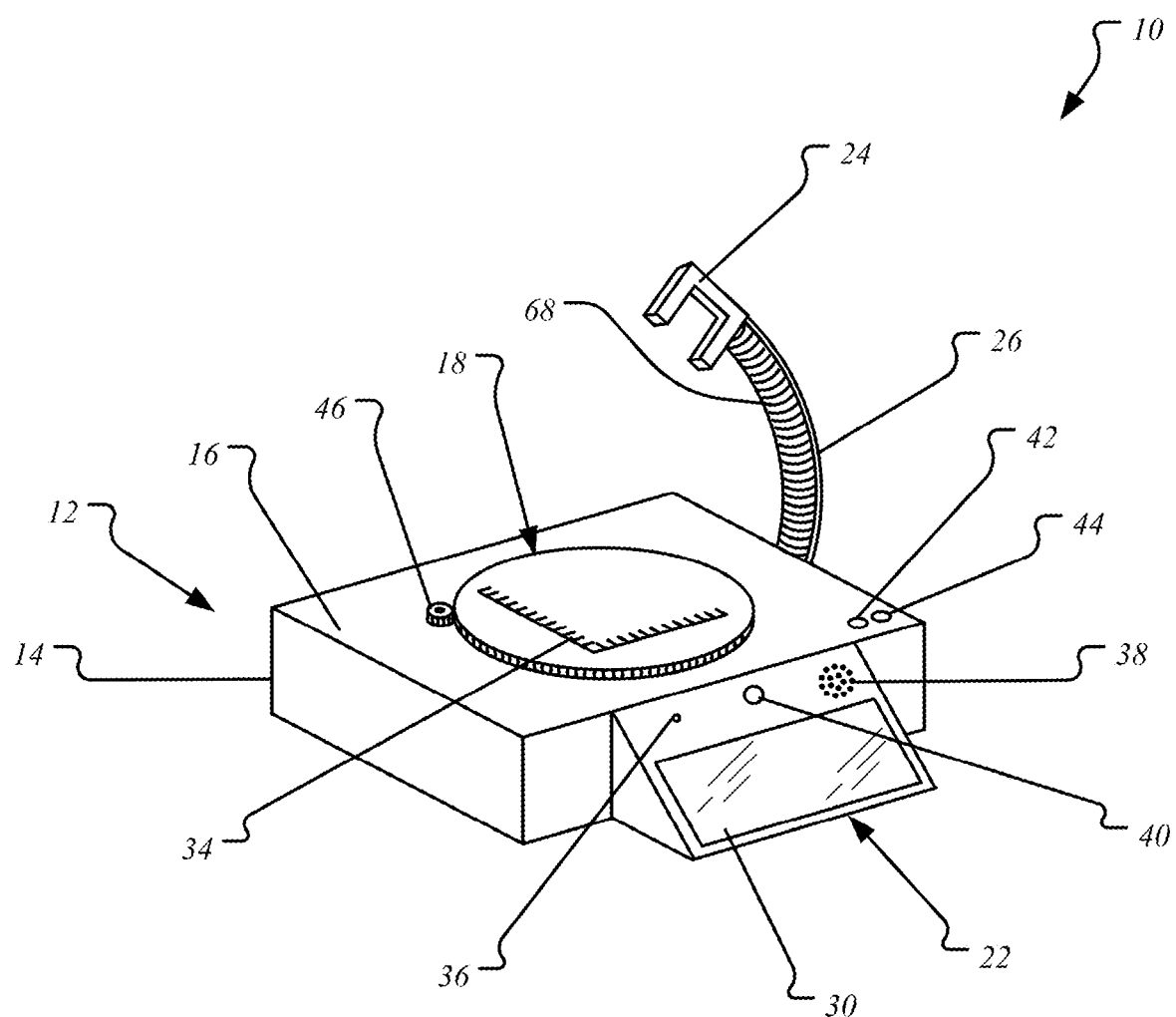
FIG. 2 shows a perspective view of a grossing workstation with a rotating balance pan and a camera holder at the end of an arcuate rack.
Figure 3:
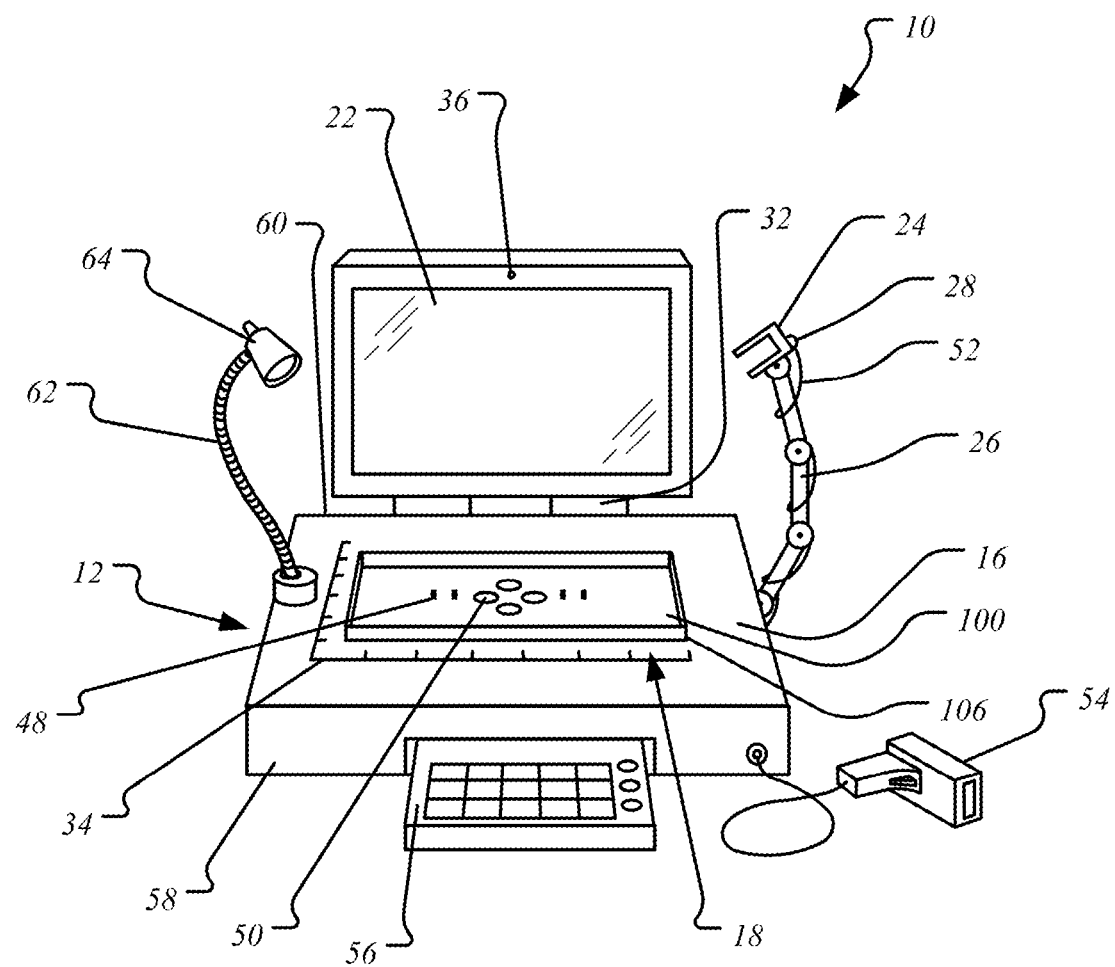
FIG. 3 shows a perspective view of a grossing workstation having a balance pan with sensors, a barcode reader, and a button panel that slides out from a first side of the housing.
Figure 4:
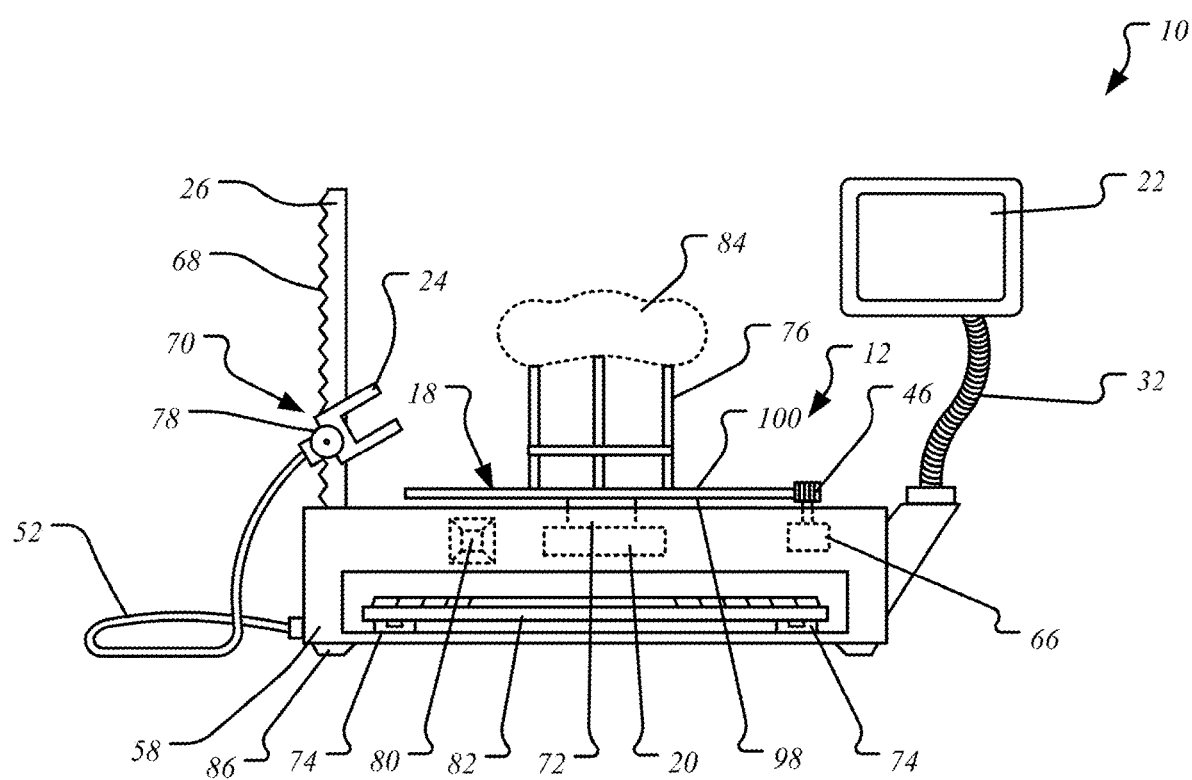
FIG. 4 shows a front view of a grossing workstation with a rack on a rotatable balance pan and a keyboard that slides out from a first side of the housing.
Figure 5:
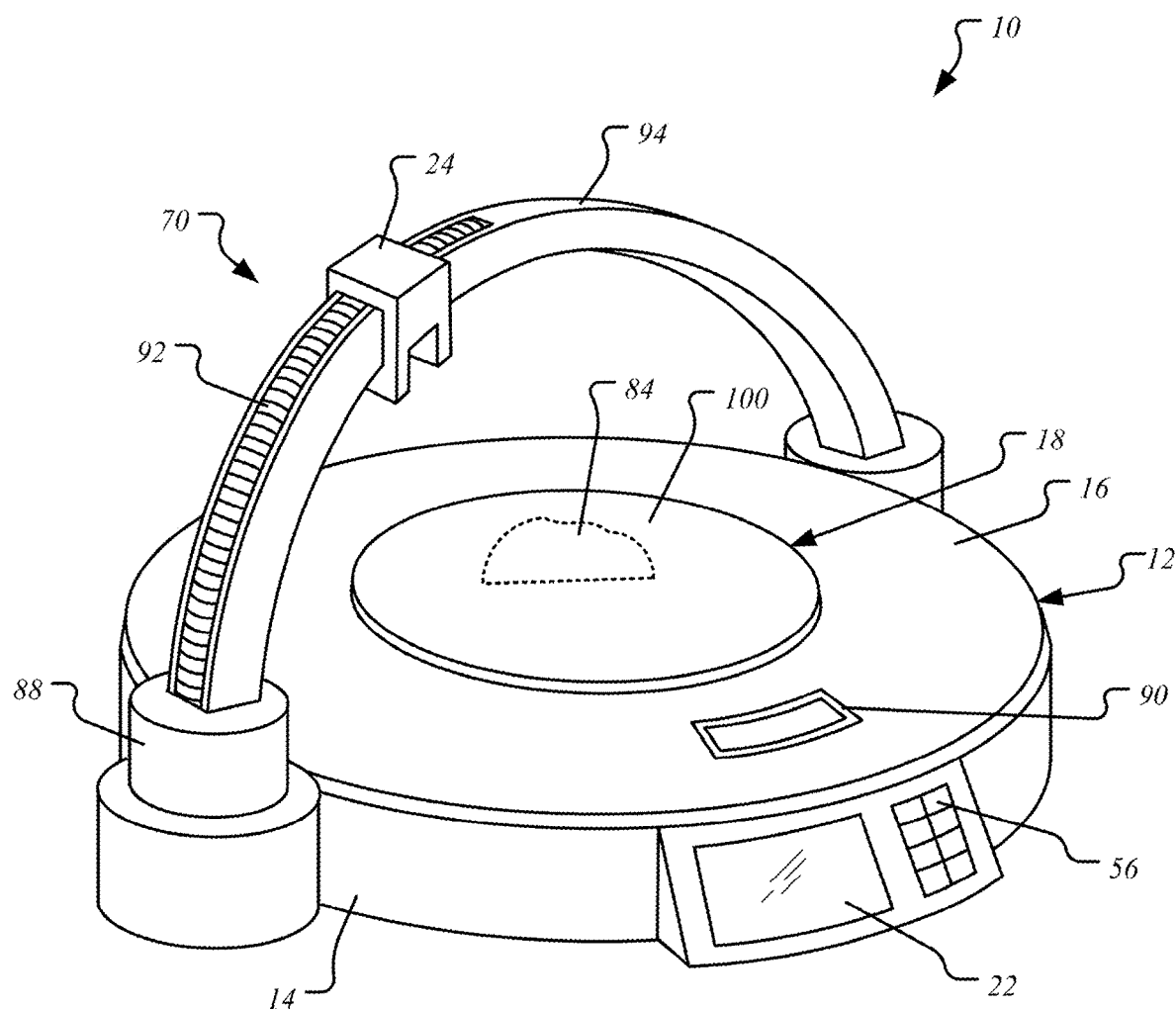
FIG. 5 shows a perspective view of a grossing workstation with a rotatable balance pan and a camera holder moveable along a portion of an arch.

Relating to these above features, FIGS. 1-5 show grossing workstations 10 having an electronic scale 12 with a housing 14 and a top side 16. A balance pan 10 is located at the top side 16, and a screen 22 is also attached to the housing. FIG. 1-4 show camera holders 24 mounted on arms, and FIG. 5 shows a camera holder 24 mounted on an arm which is in the form of an arch 94. FIG. 4 shows the computing device 80 and load cell 20 within the electronic scale, and both FIGS. 4 and 5 show a specimen 84 on the balance pan 18.

The electronic scale housing 14 may have a sidewall thickness of 0.5-4 mm, preferably 0.7-2 mm, more preferably 0.8-1.2 mm. The sidewall, as well as other parts of the grossing station, may comprise stainless steel, aluminum, nickel, cobalt, zirconium, titanium, polylactic acid (PLA), poly(lactic-co-glycolic acid) (PLGA), polyvinylchloride (PVC), polyethylene terephthalate (PET), acrylonitrile butadiene styrene (ABS), melamine, polypropylene (PP), polystyrene (PS), polytetrafluoroethylene (PTFE), polyetheretherketone (PEEK), polyetherketoneketone (PEKK), polycarbonate (PC), glass, carbon fiber, and/or ceramic. The housing 14 may have a rectangular prism shape, as in FIGS. 1-4, or may have a cylindrical shape as in FIG. 5. In some embodiments, the electronic scale 12 may have other shapes, but preferably the electronic scale housing 14 is a type of prism so that it has a bottom side in a plane parallel to a plane of the top side 16. Preferably the housing 14 has dimensions such that the grossing workstation 10 can be comfortably used after placing on a desk, tabletop, counter, pushcart, or lab bench, or after placing in a glove box or fume hood. The electronic scale 12 may have adjustable or non-adjustable feet 86 attached from the bottom of the housing to provide a level top side 16 or to keep the bottom of the housing from sitting flush against a surface. The feet 86 may have a height of 0.5-8 cm, preferably 1-3 cm, and the bottom of the feet 86 may comprise an elastomeric compound such as silicone rubber, latex, butyl rubber, neoprene, and/or nitrile. In an alternative embodiment, the housing 14 may have three or more legs of lengths 60-110 cm, preferably 70-100 cm so that the entire grossing workstation 10 may be placed on a floor. Alternatively, the electronic scale 12 may be mounted on an adjustable arm attached to a floor, wall, or ceiling. Where the electronic scale 12 has adjustable feet or legs, is attached to an adjustable mount, or placed on an adjustable surface, the electronic scale 12 may have an exterior bubble level or an interior electronic level in order to ensure level placement for accurate weight measurements. The electronic scale 12 may have a height of 1-50 cm, preferably 4-25 cm, more preferably 5-20 cm. The electronic scale 12 may have a longest lateral dimension of 20-90 cm, preferably 30-70 cm, more preferably 40-60 cm, and a shortest lateral dimension of 15-60 cm, preferably 25-50 cm, more preferably 30-45 cm. In one embodiment, the longest and/or shortest lateral dimension may be longer to provide a larger top side area for extra workspace or to accommodate larger specimens. In one embodiment, a transparent enclosure may be attached to the electronic scale 12 to cover a specimen 84 on the balance pan 18 or to cover the entire workstation 10. In related embodiments, an opaque enclosure may be used for certain optical measurements, or a shielded enclosure may be used for a procedure involving ionizing radiation. In an alternative embodiment, the workstation 10 may be integrated with a fume hood having a base area larger than the electronic scale 12. In other embodiments, a fume hood or exhaust port may extend from the top side 16 of the workstation. To enhance portability, the housing 14 may have handles so that a user may easily move the workstation 10. Likewise, a workstation housing 14 having legs configured to contact the floor, as mentioned previously, may have wheels for moving the workstation.

A balance pan 18 is located at the top side 16 of the housing. Preferably the balance pan 18 is made of stainless steel or aluminum, though the balance pan 18 may comprise any of the materials previously listed for the housing 14, and may have a wall thickness as that previously listed for the housing sidewall. Preferably the balance pan 18 has a substantially flat side, configured to contact a specimen 84.

The substantially flat side may be considered the specimen side 100, with the opposing side the bottom side 98. The balance pan 18 may be rectangular with a longest dimension of 10-80 cm, preferably 20-60 cm, more preferably 30-55 cm, and a shortest dimension of 8-70 cm, preferably 15-55 cm, more preferably 25-50 cm. The balance pan 18 may be circular with a diameter of 8-70 cm, preferably 10-30 cm, more preferably 15-25 cm, or may have some other shape such as a hexagon or ellipse with similar dimensions as those listed.

Alternatively, the balance pan 18 may have dimensions other than those listed above and may have a specimen side area that is 30-100%, preferably 40-95%, more preferably 50-90% of the total top side area. In one alternative embodiment, the balance pan 18 may extend over the top side 16 of the housing by 0.5-10 cm, preferably 1-5 cm.

As shown in FIG. 3, the balance pan 18 may have a raised lip, bead, edge, or protrusion 106 of a height 0.2-3 cm, preferably 0.3-2 cm, more preferably 0.5-2 cm from the specimen side 100 and along its perimeter to contain stray liquids from a specimen 84 or to provide a hand grip when placing or handling the balance pan 18.

In one embodiment, the balance pan 18 has one or more graduated markings 34, such as a metric ruler or some other calibration markings with fixed spacing, which are configured to measure one or more dimensions of a specimen 84. Calibration markings may be dots, boxes, grids, or other regular shapes that form part of the balance pan, such as an engraving or embossing. Alternatively, the graduated markings 34 or calibration markings may be applied to the surface of the balance pan, for example as a sticker, adhesive film, dye, or paint. In one embodiment, the graduated markings may not be on the balance pan, but on the top side 16 of the housing, along or next to the balance pan 18, as shown in FIG. 3. The graduated markings or calibration markings may extend as a line, though preferably the graduated markings or calibration markings are arranged along two perpendicular lines. These lines may each have a length of 4-75 cm, preferably 6-50 cm, more preferably 8-40 cm.

In one embodiment, the balance pan 18 may further comprise a rack 76 which is configured to elevate a specimen 84. Preferably the rack 76 is located on the specimen side 100 of the balance pan, and elevating the specimen 84 allows more of the specimen to be imaged by a camera in the camera holder, without requiring a user to manually turn or flip the specimen 84. An example embodiment is shown in FIG. 4. The bottom of the rack 76 may be welded or adhered to the balance pan 18, or may be removably attached, for instance, by a screw thread. Alternatively, the rack 76 may simply sit on top of the balance pan 18. The rack 76 may comprise three or more prongs that are connected or separated from one another, having heights of 5-15 cm, preferably 6-13 cm, more preferably 6-10 cm, diameters or widths of 1-10 mm, preferably 2-8 mm, preferably 2-5 mm, and nearest neighbor spacing of 1-10 cm, preferably 2-9 cm, more preferably 3-8 cm. Prongs that are connected to one another may be connected near their bottom, top, or middle portion by one or more wires of a similar width or diameter. The rack 76 may comprise stainless steel, or any other material mentioned for the housing 14. In one embodiment, the rack 76 may support a transparent plate or dish in which a specimen 84 is placed.

In an alternative embodiment, the rack 76 may be configured as a rotisserie to rotate a specimen 84 around a lateral axis. In this arrangement, preferably a motor is attached to drive this rotation automatically. In another embodiment, rather than a rack, the balance pan 18 has a single spindle with a pointed end with which to mount a specimen 84. In other embodiments, a user may place a specimen 84 on a disposable weighing boat, film, or paper placed on the balance pan 18.

In one embodiment, the balance pan 18 has one or more sensors electrically connected to the computing device 80 and configured to measure a physical property of a specimen 84 on the balance pan 18. The sensors may be an ultrasonic transducer 50, a spectrometer 102, a thermometer 104, or an electrode 48. An ultrasonic transducer may be used for ultrasonography imaging, or for estimating a local density of a specimen 84. The ultrasonic transducer may be piezoelectric, magnetorestrictive, or some other type, and in alternative embodiments, a transducer may create vibrations at a lower frequency than typical ultrasonic frequencies.

A spectrometer 102 may be able to measure a composition, local density, absorbance, or color of a specimen 84. In other embodiments, a specimen 84 may be dyed or selectively stained, for example, with fluorescent antibodies, that the dye or stain may be imaged by a spectrometer. As defined herein, a spectrometer is a device comprising a light source and a photodetector that together may characterize a portion of matter (solid, liquid, and/or gas) based on how the matter changes a property of the light. As defined herein, "light" refers to electromagnetic radiation within the ultraviolet, visible, or infrared wavelength ranges, which together span from 120 nm to 1 mm. The matter may change a property of the light such as intensity, direction, wavelength, and/or polarization. The spectrometer may detect these changes using detection modes such as spectrophotometry, static light scattering, dynamic light scattering, fluorescence, polarization, and/or Raman scattering. As mentioned, the spectrometer comprises one or more photodetectors, and those photodetectors may modulate an electric signal in proportion with the intensity of an incident light, with or without specificity towards the wavelength or wavelengths of the light. For example, a single photodetector may generate a similar electric signal when exposed to light of a 280 nm wavelength as for light of a 700 nm wavelength of equal intensity, or it may generate different electric signals. In one embodiment, the spectrometer is a spectrophotometer, and is able to detect a change in absorbance for an incident light having a wavelength or wavelengths in the range of 200-1050 nm, preferably 300-800 nm, more preferably 400-680 nm. Where the photodetector detects light scattering, it may measure light that is reflected back in the direction of the light beam, or deflected at an angle or range of angles, for instance, deflected 85°-95° relative to the transmission axis of the oncoming beam. In some embodiments, more than one type of photodetector may be present that together share a single light source or more than one light source. In other embodiments, different detectors may work in tandem, for instance, a photodetector for light scattering may be configured with circuitry to monitor for a sudden increase in scattering intensity.

The spectrometer's light source may comprise a gas discharge lamp, an incandescent bulb, a laser, and/or a light emitting diode (LED). The light source may be connected to the spectrometer by a fiber optic cable in order to use less space than directly attaching the light source to the balance pan 18. In an alternative embodiment, the light source may be a gas discharge lamp (such as a mercury vapor lamp, a xenon lamp, an argon lamp, or a metal halide lamp), a laser, and/or an incandescent bulb housed separately from the electronic scale housing 14, but attached by a fiber optic cable. In another embodiment the spectrometer may use ambient light, such as the light from ceiling lights, as the light source.

A thermometer 104 may be able to measure a surface temperature of a specimen, or may be configured to puncture or insert into the specimen 84 to measure an internal temperature. In one embodiment, the thermometer 104 is able to track temperature changes as a specimen warms or cools, and the computing device 80 is able to use this information to calculate a heat capacity or some other physical property of the specimen. In other embodiments, the thermometer 104 may be used to ensure that a specimen 84 does not become too warm during examination or other measurements.

In one embodiment, one or more sensors may be electrodes 48, and may have a surface comprising platinum, platinum-iridium alloy, iridium, titanium, titanium alloy, stainless steel, gold, cobalt alloy, and/or some other electrically-conductive material. As defined here, an electrically-conductive or conductive material is one with an electrical resistivity of at most $10^{-6}$ Ω·m, preferably at most $10^{-7}$ Ω·m, more preferably at most $10^{-8}$ Ω·m at 20-25° C. Preferably, where the balance pan 18 is a conducting material, the electrode 48 is electrically isolated from the balance pan 18. Alternatively, a balance pan 18 comprising ABS or some other insulating material may be used. As defined here, an insulating material is one with an electrical resistivity of at least $10^2$ Ω·m, preferably at least $10^3$ Ω·m, more preferably at least $10^4$ Ω·m at 20-25° C. In another alternative embodiment, the electrode 48 may be used with a balance pan having an electrically conductive surface. It may be configured so that an electric current is passed through the specimen 84 between the electrode 48 and some location of the balance pan. The electrode 48 may be able to measure a resistance or capacitance of a specimen 84, and the computing device 80 may be able to derive other properties from a specimen 84, such as a weight percentage of water, fat, bone, or muscle. In one embodiment, where the workstation has one or more sensors to measure a specimen 84, the workstation may also have a warning light and/or warning sound to alert a user not to handle the specimen 84 during a measurement.

In one embodiment, sensors may be elevated like prongs or comprise a part of a rack 76. For instance, a thermometer 104 may be located at the end of a prong, and the prong may be hollow for electrical wiring to be threaded through. In alternative embodiments, a sensor may be a CCD configured to detect ionizing irradiation, such as gamma rays or X-rays passing through a specimen 84. In alternative embodiments, a sensor as mentioned above may not sit on the surface of the balance pan 18 but instead may be attached at the end of a wire connected to the computing device 80. A sensor in this configuration may be clipped on or inserted into a specimen 84, or placed between the specimen 84 and the balance pan 18.

The one or more sensors may connect to the computing device 80 with an electrical connection comprising pins, screws, binding posts, springs, rings, USB connectors, coaxial power plugs, phone connectors (2.5, 3.5, or 6.35 mm), Molex connectors, FireWire connectors, banana connectors, Tamiya connectors, JST connectors, HDMI connectors, SAE connectors, registered jack (RJ) connectors, Anderson Powerpole connectors, EIAJ connectors, DIN connectors, blade connectors, crimp connectors, or other plug and socket connectors. Cables or wiring connecting the sensors to the computing device 80 may comprise a flexible single insulated wire, or an insulated braided wire of 2-10 strands. The gauge of the wire or wires may be 0-40 AWG, preferably 1-38 AWG, more preferably 4-34 AWG. In one embodiment, the wire or wires may be shielded.

A load cell 20 is disposed within the housing 14 and connected to a computing device 80. The load cell 20 is in direct or indirect contact with a balance pan 18 located on or above the top side 16 of the housing. In one embodiment, the balance pan 18 comprises a pedestal 72 extending from a central region of a bottom side 98 of the balance pan. The central region may be the area enclosed by a circle having a radius of 0.2-1.5 cm, preferably 0.5-1.0 cm from the centroid or geometric center of the bottom side. "Extending from a central region" means that a central axis of the pedestal lies within the central region. Preferably, the central axis of the pedestal intersects the geometric center of the bottom side. Preferably the pedestal 72 extends substantially perpendicularly from the bottom side 98, meaning that it forms one or more angles of 89.5°-90.5° with the surface of the bottom side. The pedestal 72 may be a prismatic shape, and in one embodiment, the pedestal 72 is a cylinder with a diameter of 0.2-6 cm, preferably 0.5-5 cm, more preferably 1-3 cm, and with a length of 0.5-6 cm, preferably 1-5 cm, more preferably 1-3 cm. In one embodiment, the pedestal 72 may traverse the housing 14 through a hole in order to reach the load cell 20. The hole may have an area 0.1-10%, preferably 1-5% larger than the cross section area of the pedestal, and may have a peripheral protrusion, raised edge, or bead to prevent liquids or debris from falling into the housing 14. This raised edge may have a height of 1-10 mm, preferably 2-8 mm, more preferably 2-5 mm above the surface of the top side 16.

The end of the pedestal 72 may sit in the load cell 20 or may be attached to the load cell 20. Preferably the pedestal 72 sits in the load cell 20 so that the balance pan 18 may be removed for cleaning or for exchanging with another balance pan 18 of a similar or different shape. In one embodiment, the pedestal 72 is configured to rotate manually or automatically while in contact with a stationary load cell 20, thus rotating the balance pan 18 and any specimen 84 placed on the balance pan 18. FIGS. 2, 4, and 5 each show workstations 10 with balance pans 18 that may be automatically rotated. In another embodiment, the balance pan 18, pedestal 72, and load cell 20 may all rotate together with respect to the housing 14. In an alternative embodiment, a pedestal 72 may be attached to the load cell 20 but rotationally attached to the balance pan 18. Here, the balance pan 18 may be rotated while the pedestal 72 and load cell 20 are stationary.

Automatic rotation of a circularly-shaped balance pan 18 may be achieved through a gear or disc 46 in contact with the balance pan's circumference and rotated by a pedestal motor 66. FIGS. 2 and 4 show embodiments of workstations 10 with this configuration. Preferably the gear or disc 46 has a diameter that is 2-40%, preferably 5-20% of the diameter of the circularly-shaped balance pan. Here, the gear or disc 46 may have gear teeth that meld with gear teeth on the circumference of the balance pan, or the gear or disc may comprise an elastomeric compound, such as those listed previously for the housing feet 86, that presses against the circumference of the balance pan to provide a frictional coupling. In this embodiment, the gear or disc 46 and its pedestal motor 66 may be moveable between the position in contact with the balance pan 18, and a position out of contact with the balance pan 18. Moving the gear or disc 46 to the position out of contact with the balance pan 18 may be done prior to weight measurement or removing the balance pan 18. This moving may be done manually or automatically. In another embodiment, one or more idle gears may transfer the movement from the pedestal motor to the circularly-shaped balance pan. In other embodiments, the gear or disc may be part of a belt drive or a chain drive. Preferably in this arrangement, the electronic scale 12 is able to properly zero and measure a specimen 84 without having to remove the belt or chain.

In an alternative embodiment, a balance pan 18 may not have a pedestal 72 and may instead sit flush against a load cell 20. In this embodiment, the top side 16 of the housing 14 may have a hole or cutout with an area 0.1-1%, preferably 0.2-0.8% larger than the area of the balance pan 18. In this embodiment, the balance pan 18 may be positioned with its specimen side 100 above the plane of the top side, below the plane of the top side, or within the plane of the top side.

The load cell 20 is configured to translate a force on the balance pan 18 into an electrical signal which is sent to the computing device 80. The load cell 20 may be a strain gauge load cell, a capacitive load cell, a piezoelectric load cell, a pneumatic load cell, a hydraulic load cell, or a fiber optic load cell. A strain gauge load cell uses the force from the balance pan and specimen to deform one or more strain gauges. A strain gauge is a conductor that changes its resistance when deformed. One or more strain gauges may be connected to circuitry, such as an amplifier, to increase the strength of the electrical signal. In one embodiment, a load cell 20 may use four strain gauges in a Wheatstone bridge configuration. A capacitive load cell 20 and piezoelectric load cell 20 may also be used with respective sets of capacitive or piezoelectric strain gauges. A capacitive strain gauge creates a variable capacitance that is detected, and a piezoelectric strain gauge creates a variable voltage that is measured. In alternative embodiments, a pneumatic or hydraulic load cell may be used, which transfer a measurable pressure change through a fluid. In another alternative embodiment, a fiber optic sensor may be used where a force on one or more optical fibers actively transmitting a light changes a property of the light, such as intensity, polarity, or propagation direction, that may be quantified by detection circuitry.

Preferably the load cell 20 is a compressive strain gauge load cell and may further comprise a spring in order to mitigate the direct force from a specimen 84 on the balance pan 18. The load cell 20 may also be configured with a mechanical damper to decrease longitudinal vibrations when a specimen 84 is placed on or removed from the balance pan 18.

The load cell 20 may be able to measure specimen weights of 0.01 g-5 kg, preferably 0.05 g-1 kg, more preferably 0.1 g-500 g with readability intervals of 0.001-5 g, preferably 0.01-1 g, more preferably 0.05-0.5 g.

In one alternative embodiment, the balance pan 18 may have more than one pedestal, for example, a rectangular balance pan may have four pedestals, each located near the corners of the balance pan.

In one embodiment, the balance pan 18 may be in contact with one or more load cells located away from a central area of the balance pan. The central area, or the entire balance pan 18, may be optically transparent. Then, a camera or some other optical sensor may be disposed below the central portion, in order to image or detect a property from a surface of a specimen 84 in contact with the balance pan 18.

In one embodiment, where the balance pan may be interchanged, the balance pan 18 may have an identifier, such as a graphical feature like a barcode, machine readable text, or a QR code, or may have an internal identifier, such as an RFID tag. A circuit in the electronic scale 12 or a camera in the camera holder 24 may be able to identify the balance pan 18, and automatically tare or zero the weight measurement before a specimen 84 is placed on the balance pan 18. This automatic tare or zero feature may be manually overridden if a user wishes to place a specimen 84 on weighing paper or in a container on the balance pan 18. In addition, by identifying the type of balance pan, an electronic scale 12 may be able to detect and record measurement drift or noise from the load cell 20.

The camera holder 24 is configured to secure and electrically connect with a digital camera to image a specimen 84 on the balance pan 18. Preferably the camera holder 24 is configured to hold a digital point-and-shoot camera; however, in some embodiments the camera holder 24 may be able to hold a smartphone or small tablet computer that has a camera. In other embodiments, the camera holder 24 may be able to hold a single lens reflex camera (SLR) or a digital SLR camera (DSLR). Preferably where the camera holder 24 is configured to hold heavier cameras such as SLR or DSLR, the arm 26 is supported from its distal end or forms an arch 94, as in FIG. 5. The camera holder 24 may secure a camera with a screw (such a ¼"-20 or ⅜"-16 screw used in common camera mounts), a clutch, a clip, a latch, a flexible strap, a frictional coupling, a magnetic coupling, or a clamp. The camera holder 24 may be made out of any of the materials previously mentioned for the housing 14 and may have a base with a length of 4-20 cm, preferably 5-18 cm, more preferably 6-14 cm and a width of 1-8 cm, preferably 1.5-7 cm, more preferably 2-6 cm. From the base, one or more protrusions may extend and may be configured to contact the sides or edges of a camera. These protrusions may be thought of as a frame to secure the camera. These one or more protrusions may have a length of 2-12 cm, preferably 3-10 cm, more preferably 4-8 cm, and a width of 0.1-3 cm, preferably 0.2-2.5 cm, more preferably 0.5-2 cm, and a sidewall thickness of 0.1-1 cm, preferably 0.2-0.4 cm. In some embodiments, such as where a camera attaches to the base by a camera mount screw, the camera holder 24 may not need a frame on the base secure the camera. In a related embodiment, a plate may be attached to a camera by a ¼"-20 or ⅜"-16 screw, and this plate may removably attach to the camera holder 24. In this embodiment, the plate may also be known as a "quick release plate." In other embodiments, one or more parts of the camera holder 24 configured to contact a camera may have a surface comprising a cushioning material. This cushioning material may comprise a plastic foam or an elastomeric compound as mentioned previously. In one embodiment, one or more pieces of plastic foam or elastomeric compound may be placed inside a camera holder 24 as shims or spacers to secure a camera that would otherwise be loose or not fit.

The camera holder 24 is attached to the housing 14 by an arm 26, and is electrically connected to the computing device 80. In one embodiment, a camera holder 24 may comprise one or more lenses to change the imaging properties of a camera. For instance, a small camera or smartphone may fit in a camera holder 24 that supports additional lenses. In another example, the camera holder 24 may support a dichroic filter to enable fluorescent imaging. In a further embodiment of this example, one or more dichroic filters may be housed on a wheel or a switchable mechanism in order to change imaging modes. A camera with a dichroic filter may be able to image a specific fluorescent staining on a specimen 84, for example, with fluorescent antibodies. Here, the illumination source may be a UV light, and may be attached to the housing 14 or located separately.

Preferably the camera holder 24 has an electrical connector such as those mentioned previously for the sensors and input devices, or may have something different, such as a plug that fits into a memory card slot on a camera. Preferably the electrical connection is able to send captured images from a camera to the computing device 80. These captured images may be in file formats such as JPEG, JPEG 2000, Exif, TIFF, GIF, BMP, PNG, WebP, PSD, or some other file format. Additionally, the electrical connection may allow the computing device 80 to control certain operations of the camera. For instance, the computing device 80 may be able to control the image capture, focus, exposure, depth of field, resolution, color balance, image size, zoom, or frame rate of a moving image or movie. This controlling may be done through an input device, controls on the camera directly, or through controls on the camera holder 24 connected to a camera. In one embodiment, the camera has a button 28 or switch to cause a camera to take an image. In a further embodiment, triggering this button 28 or switch begins an automatic imaging routine.

The electrical connector may be fixed to the camera holder 24 and immovable, or may be attached to the camera holder 24 by a short piece of cable, for instance, 1 cm-12 cm, preferably 3-10 cm in length. In one embodiment, that electrical connector, or an additional electrical connector, is able to power and/or charge a camera. In another embodiment, a camera may be controlled by or transfer images through a wireless connection with a workstation further comprising a wireless transceiver. The wireless connection may be made through a wireless transmission protocol such as 802.11x, CDMA, IS-136, Bluetooth, Bluetooth low energy, Ultra-wideband, GSM, 6LoWPAN, 802.15.4, ANT, DASH7, ISA100.11a, MiWi, near-field communication, OCARI, ONE-NET, TSMP, WirelessHART, ZigBee and/or Z-Wave, or some other wireless transmission means.

In an alternative embodiment, the workstation may have one or more built-in cameras, which may be arranged or attached to the workstation in a manner similar to the camera holder 24, as mentioned previously. In another alternative embodiment, the camera holder 24 may be able to hold and take images with a camera containing 35 mm film, or some other camera film. The camera may be a single lens reflex (SLR) or a point-and-shoot camera, and the camera functions may be controlled through the computing device 80 or camera holder 24.

The arm 26 may have a length of 10-60 cm, preferably 15-50 cm, more preferably 20-45 cm. As defined here, the arm is an elongated structure supported or attached from one or more ends and designed to hold a load in a static position. In one embodiment, the arm 26 is flexible or articulating. A flexible arm may have an adjustable curvature along its length with a minimum bending radius of 1-30 cm, preferably 3-20 cm, more preferably 4-15 cm, which may be possible with a gooseneck tubing similar to those used in desk lamps and microphone holders. Alternatively, the flexible arm may have a series of ball and socket joints along its length, or may have an elastomeric tubing with a position supported by one or more flexible metal wires. An articulating arm may have 1-5, preferably 2-4 adjustable or articulating joints, which may be hinges or ball and socket joints. FIGS. 1 and 3 show workstations 10 each with an arm 26 having articulating joints. In one embodiment, an articulating arm with moveable joints may have one or more joints with adjustable tension, for example, by a nut or wingnut. In another embodiment, a segment of an articulating arm between two joints may form a parallelogram or pantograph structure. The camera holder 24 and arm 26 may connect with a hinge or a ball-and-socket. In one embodiment, a flexible or articulating arm may enable a camera holder 24 to point a camera in any direction.

In one embodiment, an articulating arm may have one or more mechanisms or structures attached to one or more joints to support the weight of a camera in the camera holder 24, similar to a balanced-arm lamp. These mechanisms include a pneumatic cylinder, a hydraulic cylinder, a gravity-locked elbow, a cam-locked elbow, a torsion spring, a compression spring, and a counterweight. In a further embodiment, a motor may be able to pivot the camera to different view angles, without otherwise changing the height or location of the camera. For instance, in FIG. 4, one motor 78 may be able to move the camera up and down on the arm 26 while an additional motor is able to independently change the camera angle.

In one embodiment, the base of the arm may be rotatably attached to the housing 14, though in other embodiments, the base of the arm may be attached in a fixed position. In one alternative embodiment, the base of the arm may be attached to a track on the housing circling a balance pan. In this alternative embodiment, the balance pan 18 may remain stationary relative to the housing, while the arm 26 is able to rotate around the balance pan 18, and the camera holder 24 is able to move up and down and/or along an arc.

The camera holder 24 may connect to the computing device with a data cable disposed within the arm, attached to the outside of the arm, or wrapped along the length of the arm. FIG. 3 shows a data cable 52 wrapped along the length of the arm 26.

As mentioned previously, the screen 22 may be attached to the housing 14 by an adjustable mount. In one embodiment, the adjustable mount may be a flexible or articulating extended structure, with properties or construction similar to those mentioned above for the flexible or extended arm 26. For instance, FIG. 4 shows a screen attached by an adjustable gooseneck tubing.

In one embodiment, the camera holder 24, arm 26, or both comprises a motor and an actuator 70. The actuator 70 is a mechanism or set of mechanisms that converts the rotational motion of the motor into translational motion on the camera holder 24, arm 26, or both. In one embodiment, this actuator 70 may be a lead screw, a belt drive, a worm drive, a rack and pinion drive, and/or a chain drive. The translational motion may be on a linear or curved path, which path may depend on the shape of the arm 26. For instance, FIG. 4 involves movement on a linear path while FIGS. 2 and 5 involve movement on curved paths. Preferably the electric motor runs on DC power. The electric motor may be a brushed or brushless DC motor, a switched reluctance motor, a universal motor, a stepper motor, a servomotor, an axial rotor motor, or some other type of motor. In an alternative embodiment, the motor may be an AC asynchronous motor, such as a shaded pole motor, or an AC synchronous motor, such as a hysteresis motor, or some other AC motor. Preferably, a gear train may exist to reduce the rotational motion coming directly from the electric motor. In an alternative embodiment, a portion of the arm 26 may have a telescoping segment, with or without an actuator 70, to extend or retract the length of segment. In another alternative embodiment, a camera holder may be moved with a motor and a rigid belt actuator, push-pull belt actuator, or a rigid chain actuator.

In a further embodiment, the motor may receive an electrical signal from the computing device 80 to move the camera holder 24 in a particular direction or to a particular position. In a further embodiment, where the camera holder 24, arm 26, or both comprises a motor and an actuator 70 for automatic movement of the camera holder 24, the camera holder 24 may also be manually moveable. In that embodiment, a user may be able to position the camera holder 24 without the motor's operation. Additionally, in the embodiments where the camera holder is moveable by a motor, preferably a feedback circuit or mechanism allows the computing device to determine the position of the camera holder. In related embodiments, a motor may have a self-calibration routine, for instance, the motor may move the camera holder between extreme positions along an arm, such as from a proximal end on a track to a distal end.

FIG. 2 shows an example of a camera holder 24 fixed in relation to an arm 26. Here, the arm 26 is curved with a track of gear treads 68 along its length on the inside of the curve. The motor within the housing 14 connects to the arm 26 making a rack and pinion actuator, with the arm 26 as an arcuate rack. The rotation from the motor is able to extend or retract the arm 26, while a camera in the holder is continually aimed towards the balance pan 18 due to the arm's curvature.

In one embodiment, the motor may be attached to or fixed in a position with the camera holder 24, so that both motor and camera holder 24 may translate on an arm 26. For example, FIG. 4 shows an arm 26 fixed vertically to the housing 14 and having a gear track 68. The motor 78 is attached to and moves with the camera holder 24. In this embodiment, the angle of the camera holder relative to the arm may be adjusted by an additional motor. With this additional motor, the angle of an attached camera may be automatically changed while the camera is moving vertically, in order to keep the camera aimed at a specimen 84 on the rack 76.

In embodiments where the arm 26 has a track 68 along a portion of its length to form an actuator 70 with a gear (for example, the arm 26 of FIG. 4), the track 68 may be on any side of the arm 26 for both curved and straight arms. In a further embodiment, the arm 26 may have more than one track 68 along its length, for example, on opposite sides.

In one embodiment, to ensure stability of a camera in the camera holder 24, an arm may be attached to the housing 14 at both ends, forming an arch 94. Alternatively, the distal end of an arm may be supported by a second arm or some other structure. Thus, an arch or arched structure may be considered to consist of one or two arms. An arch may have a total length similar to that mentioned previously for the arm, or may be 20-150%, preferably 30-100%, more preferably 40-70% longer. The arch 94 may curve with a circular curve, a parabolic curve, a hypercosine curve, a parametric curve, or some other curved shape. In one embodiment, the arch has a circular curve with the balance pan 18 or a specimen 84 on the balance pan coinciding with the center of the circle. Where a camera holder is movably attached to an arch 94, a camera may be moved stably over the top of the balance pan 18, whereas an arm supported or attached at only one end may sag or shake. Preferably, in this embodiment, the arch 94 is not flexible or articulating. FIG. 5 shows an example of an arm forming of an arch 94 above and over a balance pan. Here, the camera holder 24 is moved on the arch 94 by a screw drive within a track or slot 92 on a portion of the arch. This arrangement is similar to a traveling nut linear actuator. Here, the screw drive is also flexible so that it may be rotated within the arch 94 by a motor 88 located at one end of the arch. As the balance pan 18 is rotatable, the camera holder 24 only needs to translate up one half of the arch or less in order to completely image all exposed exterior surfaces of the specimen 84. As such, the slot 92 in FIG. 5 terminates near a top portion of the arch. In the embodiment depicted in FIG. 5, the arch 94 has a similar cross-section area throughout its curve, however, in other embodiments where the camera holder 24 translates on only a portion of an arch, the portion of the arch that does not have a slot or track may have a smaller cross-section area, for instance, 20-80% smaller, or 30-70% smaller, or have a different shape. In an alternative embodiment, three arms may extend from an electronic scale housing 16 and form a curved tripod shape that meets above a balance pan. In one embodiment, where a camera holder 24 is supported by an arch 94, or two or more arms, the arch or the two or more arms may be articulating or flexible, as described in a previous embodiment for the arm 26.

In a related embodiment, a camera holder 24 may be attached to an arm in the form of a circular arcuate rack. This circular arcuate rack forms a complete circle in a plane substantially perpendicular to the specimen side 100 of the balance pan. The circle may have an inner diameter of 15-90 cm, preferably 20-80, more preferably 30-70 cm, and the outer diameter may be larger by 1-8 cm, preferably 2-6 cm, more preferably 2.5-5 cm. This circular arcuate rack may have gear treads 68 on the inside or outside of the curve. A motor in the electronic scale housing may connect with gear teeth to rotate the circular arcuate rack, which then is able to move an attached camera holder up and over the balance pan. In this embodiment, the housing 14 of the electronic scale may have a larger height than that mentioned previously to accommodate a bottom portion of the circular arcuate rack. Alternatively, the housing 14 may be supported on legs as mentioned previously, and the bottom of the housing may have an opening for the arcuate rack to protrude. A portion of the circular arcuate rack above the electronic scale 12 may be housed in an arched housing that has a slot along its inner curve for accommodating a camera holder 24. In this embodiment with a circular arcuate rack, a counterweight may be added to balance the torque from a camera attached to the camera holder 24. A circular arcuate rack may be able to move a camera along an arc from one end of the housing to a distal end of the housing, while keeping a camera aimed at a specimen 84 or a central portion of the balance pan 18.

In one embodiment, grossing workstations that have camera holders automatically moveable along one direction or along one curve, as in FIGS. 2, 4, and 5, also have balance pans 18 that can be automatically rotated in tandem. This configuration allows imaging of all exposed exterior surfaces of a specimen. In other embodiments, a balance pan 18 may not be rotated, and instead a camera holder 24 may be moveable in more than one direction or along a winding path that allows all exposed surfaces of a specimen 84 on the balance pan 18 to be imaged. In another embodiment, grossing workstations that have camera holders automatically moveable along one direction or along one curve may have a rotisserie style rack configured to rotate a specimen, as mentioned previously. Alternatively, a rotisserie style rack on a rotatable balance pan may be used with a camera in a fixed position.

The electronic scale 12 also has a screen 22 attached to the housing 14 and electrically connected to the computing device 80. The screen 22 may comprise one or more LEDs, organic light-emitting diodes (OLEDs), active-matrix organic light-emitting diodes (AMOLEDs), liquid crystal display (LCD) cells, E ink cells, quantum dots, incandescent bulbs, cathode ray tubes, lasers, plasma cells, and/or gas discharge lamps. A screen comprising an LCD or E ink element may optionally be backlighted.

The screen 22 may form a numeric or alphanumeric display, or may otherwise indicate information by being in an on/off state, for example, if having an illuminated element located next to a label. The screen 22 may indicate specimen weight or other properties measured by sensors, such as a weight percentage of water. Additionally, the screen 22 may indicate a status of the grossing workstation 10, such as a power state, camera connection, available storage space, data transfer, network connection, tare weight, image rate, rotation speed, specimen number, date, time, case number, operator name, illumination status, or some other information.

In one embodiment, the screen 22 is an LED screen with a plurality of LEDs that form pixels of an image. An LED screen may have a 2D array of at least 625 LEDs, preferably at least 1,000 LEDs, more preferably at least 5,000 LEDs. In one embodiment, the LED display may be similar to a modern computer LED monitor screen, tablet screen, and/or smartphone screen and may produce at least 100 pixels per square inch (PPI), preferably at least 200 PPI, more preferably at least 300 PPI. The image formed may be monochromatic, or multicolored LEDs may be used to produce images of more than one color. The LEDs may be configured to emit light at only one power intensity, or they may be configured to emit light at more than one intensity. In one preferred embodiment, the LED display is able to show images captured by a camera in the camera holder 24. In another embodiment, the LED display may show an image computed by the computing device 80, or a graph from data received by one or more sensors.

The screen may have a width of 2-25 cm, preferably 3-20 cm, more preferably 4-15 cm, and a height of 2-20 cm, preferably 3-15 cm, more preferably 4-12 cm. In one embodiment, the screen 22 may have a resolution and/or size similar to a smartphone screen, a tablet screen, or a computer monitor screen. In embodiments where the screen is large, for example, having a viewable surface area larger than 45 $cm^2$, preferably larger than 50 $cm^2$, the screen may be attached to the housing 14 by a hinge or adjustable mount 32, preferably on a side of the housing away from the position of a user. In another embodiment, a screen 22 may be integrated with the housing 14, as FIGS. 2 and 5. Here, the screen 22 is on a slanted portion of the housing 14 in order to increase visibility. In one embodiment, a grossing workstation 10 may comprise two screens, such as a screen located on a side of the housing 14 close to a user, and a second screen attached to an adjustable mount. Preferably the second screen is larger and configured to display images taken by a camera in the camera holder 24, while the first screen is used to show measurement and control parameters. The first and/or the second screen may be touchscreen 30. Preferably a grossing workstation that has a screen to show specimen images also has a video output connection, such as HDMI, RCA, VGA, mini-VGA, DisplayPort, S-Video, or DVI, in order to display the images on a separate monitor or on a projection screen. In another embodiment, the screen may be able to display stereographic 3D images, or the computing device may output such images to a separate monitor, projector, hologram projector, or headset.

In one embodiment, the screen 22 may be a touch-sensitive screen or touchscreen 30, as in a tablet computer touchscreen or a smartphone touchscreen. In this embodiment, a button panel 56 or keyboard 82 may not be necessary, as the touch-sensitive screen 30 may also work as a primary interface for operating the workstation.

In one embodiment, the screen 22 and camera holder 24 may be positioned so that a camera can image both a specimen 84 and the screen in a single shot. Here, the screen 22 may display the specimen's weight, case number, or other identifying information, so that a single image may be sufficient to see a specimen and its weight or identifying information. In related embodiments, a weight measurement or other information may be displayed on the housing 14, and a camera in the camera holder 24 may simultaneously image both the displayed information and the specimen. In another related embodiment, a digital image of the specimen may be appended or overlaid with a weight measurement, or a weight measurement may be stored in the metadata of a digital image file.

In one embodiment, the grossing workstation 10 further comprises at least one input device electrically connected to the computing device 80. The input device may be connected by a connector similar to that mentioned for connecting the sensor to the computing device 80. In a further embodiment, the at least one input device is a microphone 36, a barcode scanner 54, an infrared camera 40, an RFID tag reader 90, a keyboard 82, a mouse, a joystick, a button panel 56, a touch pad, or a touchscreen 30. The microphone 36 may be located on, within, or just inside the housing. FIG. 2 shows a workstation with the microphone 36 located just inside the housing 14. Alternatively, the microphone 36 may be located on a structure extending from the housing 14, such as the arm 26 of the camera holder 24, a screen 22 mounted on the housing 14, or an additional adjustable arm. For example, FIG. 3 shows a microphone 36 located above a mounted screen 22. The microphone 36 may be a condenser microphone, an electrostatic microphone, or some other kind of microphone. The microphone 36 may be configured to record observations from a user, or to take vocal commands for operating the grossing workstation 10. Recorded observations may be stored as audio files or further processed into text files by speech recognition. In another embodiment, a user may verbally input a case name or a specimen name using the microphone 36. In another embodiment, an external microphone or headset may be connected to the housing through a microphone jack, which may be a 2.5 or 3.5 mm phone connector, or some other connector as mentioned previously.

In one embodiment, the input device may be a barcode scanner 54. This may be used to scan a case file name on a physical tag, label, or file folder. The barcodes may be a 1D (linear) pattern or a 2D pattern (for example, QR codes). The barcode scanner may be a handheld device, as shown in FIG. 3, or may be integrated with the electronic scale housing 14. The barcode scanner 54 may use a scanning laser, a camera, or a light pen to read barcodes. In an alternative embodiment, a camera attached to the camera holder 24 may image a barcode which is interpreted by the computing device 80.

In one embodiment, the input device may be an infrared (IR) camera 40. A user may be able to control the operation of the workstation, such as initiating or stopping an imaging routine with certain hand gestures in front of the IR camera. This enables hands-free operation of the workstation, which may be useful for a user in the middle of a forensic autopsy procedure in which they don't want to repeatedly remove and replace gloves. In one embodiment, an IR camera 40 may be paired with an IR source to increase sensitivity. For example, the infrared source may be an infrared LED or infrared scanning laser. In another embodiment, a workstation may have two or more IR cameras for depth detection. In another embodiment, an optical camera may be used to detect and interpret hand gestures.

An RFID tag reader 90 may be integrated with the electronic scale housing 14 or connected in a separate housing. In another embodiment, an RFID tag reader 90 may be integrated with the balance pan 18. FIG. 5 shows an RFID tag reader 90 integrated with the top side 16 of the housing. The RFID tag reader 90 may read tags attached to or inserted within a specimen 84, or may read a tag on a physical file folder to identify case information for automatic data entry or electronic file management. In one embodiment, an RFID tag reader 90 may read a certain tag to identify a user and/or enable a workstation to be used.

Other methods of automatic identification and data capture (AIDC) may be used besides barcodes and RFID tags, for example, optical character recognition, handwriting recognition, or magnetic stripes. Optical character recognition and handwriting recognition may be done through a camera attached and integrated with the housing 14, or with a camera attached to the camera holder 24. A magnetic stripe may be located on a physical case file folder or may be located on a user's identification card. A magnetic stripe reader may be integrated with the housing 14, or may be located within a separate housing and attached to the electronic scale 12 by a data cable.

In one embodiment, the input device may be a keyboard 82 or a button panel 56. The keyboard 82 may be similar to a desktop computer keyboard, a laptop keyboard, or a portable keyboard for use with a tablet computer. The keyboard 82 may have a longest dimension of 10-50 cm, preferably 15-40 cm, more preferably 20-35 cm, and a shortest dimension of 6-25 cm, preferably 7-22 cm, more preferably 8-17 cm. Preferably the keyboard 82 is spill resistant or sealed with a flexible, transparent film. The button panel 56 comprises a substantially flat arrangement of 2-28, preferably 4-25 buttons. The button panel 56 may have a longest dimension of 4-30 cm, preferably 5-25 cm, more preferably 6-22 cm and a shortest dimension of 3-28 cm, preferably 4-20 cm, more preferably 5-15 cm. In some embodiments the button panel 56 may have LED lights to indicate information about a process or to show that a certain button was depressed and triggered. This may be similar to the Lighted Program Function Keyboard (LPFK) produced by IBM.

In one embodiment, the keyboard 82 and/or button panel 56 may be incorporated with the housing 14 in a fixed position. Alternatively, the keyboard 82 and/or button panel 56 may be hingedly attached to the housing 14, or connected to an adjustable mount, as mentioned previously for the screen 22. In one embodiment, a button panel 56 may be located adjacent to a screen 22 on an electronic scale 12, as shown in FIG. 5. Alternatively, the keyboard 82 and/or button panel 56 may be located in a separate housing 14 and electrically connected by a cable.

In one embodiment, an input device may be a stylus or pen with a pressure sensitive tip. Dragging the tip over a specimen 84 may enable a computing device 80 to identify a surface of a specimen. Geometric coordinates may be interpreted from this stylus or pen, and the data may be combined or corroborated with image calculations. Alternatively, a stylus or pen may be able to detect rigidity at different points on a specimen, or may house a sensor similar to those mentioned for the balance pan, such as an electrode.

In one embodiment, a keyboard 82, a touchscreen 30, a button panel 56, or some other substantially flat input device, may be slidably attached to one or more rails 74, preferably two rails 74. The input device may have a first position within the interior of the housing 14, and a second position extending from a first side 58 of the housing 14, the first side 58 being where a user would stand. The one or more rails allow the input device to slide between the two positions. These rails may also be called "slides." In one embodiment, the one or more rails 74 may be similar to drawer slides within a piece of furniture. The input device may be placed on the one or more rails 74 with or without wheels or ball bearings. The length of sliding between the two positions may be 5-30 cm, preferably 10-25 cm, more preferably 12-20 cm. Preferably the first position places the input device below the load cell 20, and out of the path of liquids that may spill from the top side 16 of the housing or balance pan 18. In this configuration, the top side 16 of the housing, with or without the balance pan 18, may be sprayed or rinsed for cleaning, without liquids dripping or spilling from the top side 16 of the housing onto the input device. In one embodiment, when the input device is in the first position, the exterior part of the input device may sit flush against the first side 58 of the housing 14. In this embodiment, the input device may have a tab, handle, knob, or depression for a user to manually pull out the input device to the second position. Alternatively, the input device may have a spring lock, where the input device may be pushed in slightly to release the locking mechanism, similar to a "push to open" latch. In one embodiment, the sliding movement may be caused by an additional motor and a linear actuator.

In one embodiment where a keyboard 82, touchscreen 30, button panel 56, or some other input device is slidably attached to one or more rails to slide in and out of the housing interior through a first side 58 of the housing, the screen 22 is attached to a second side 60 of the housing opposing the first side 58. An embodiment of this arrangement is shown in FIG. 3, where the balance pan 18 is located between the screen 22 and the button panel 56. This arrangement enables easier viewing of the screen 22, and comfortable operation of the input device, without requiring a user to reach over a specimen. In a related alternative embodiment, the screen 22 may instead be attached to the top side 16 of the housing, on a portion of the top side opposing the first side 58. In a further embodiment, the screen 22 is attached to the second side 60 of the housing 14 by a hinge or an adjustable mount 32. This is also shown in FIG. 3. In a related embodiment, a keyboard 82, touchscreen 30, or button panel 56 may slide from a first side 58 of the housing 14, but the screen 22 may be mounted on some other side of the housing, such as the right side or left side, or the screen 22 may be mounted to the top side 16 of the housing near the right side or left side. This embodiment is shown in FIG. 4, where the screen 22 is mounted on the right side of the housing.

Other input devices may include a computer mouse, a track pad or touchpad, a joystick, a track ball, a foot-operated switch or pedal, a fingerprint scanner, and a digital pen. Any of the described input devices may be integrated with the electronic scale housing 14 or attached by a cable. In other embodiments, one or more input devices may not be physically attached to the electronic scale 12 but instead interface through a wireless protocol, such as those mentioned previously.

The grossing workstation 10 may have other output devices, such as a speaker 38, an indicator light, or a printer. A speaker 38 may be used to play audio from a previously recorded observation in a case file, or a speaker may alert a user to a certain parameter or process underway. For instance, the speaker 38 may generate a sound to alert that an imaging procedure has begun, or may generate a warning sound if a maximum weight has been detected on the load cell 20. For simple alerting sounds, a buzzer may be used instead of a speaker. The speaker 38 may be electrostatic or magnetostatic. In a related embodiment, the housing 14 may have an audio jack, such as a 2.5 or 3.5 mm phone plug, to allow external headphones or speakers to be connected. In one embodiment, the housing 14 may have one or more indicator lights to generate alerts or warnings for similar reasons as those mentioned for the speaker 38. The indicator lights may contain an illumination element as mentioned previously for the screen 22, and in one embodiment, indicator lights may be located on the arm 26 or the camera holder 24. In a preferred embodiment, an indicator light may indicate that the workstation is powered and/or plugged in. In an alternative embodiment, the workstation may have a printer to print images, or to print information relating to the case file or other measurements. As mentioned previously for the input devices, these output devices may be integrated with the housing 14 or located separately, having a cable attachment.

In one embodiment, the grossing workstation 10 has a second arm 62 attached to the housing 14. This second arm 62 has one or more lights configured to illuminate a specimen 84. In a related embodiment, the arm 26 and/or the camera holder 24 may have one or more lights to illuminate a specimen. The lights may be any of those listed for the spectrometer light source, but preferably the lights are LEDs, or gas discharge lamps such as fluorescent lamps or halogen lamps. In one embodiment, a light may be a mercury discharge lamp, configured to emit a germicidal UV light onto a surface of the grossing workstation 10. In one embodiment, the light to illuminate the specimen 84 may be controlled by a button panel 56, a touchscreen 30, or a button or switch on the light itself or on the housing 14. In another embodiment, a light setting may automatically adjust based on an external light sensor or based on an image captured by a camera in the camera holder 24. In another embodiment, a screen 22 that faces the balance pan 18, such as the screen 22 in FIG. 3, may be used to illuminate a specimen 84. In another embodiment, a second arm 62 with one or more lights may function as a light source for a spectrometer 102 in the balance pan 18.

As mentioned previously, the workstation has a computing device 80 disposed within the housing 14 and electrically connected to the load cell 20. This computing device 80 may control a camera, the camera holder position, and the rotation of the balance pan. The computing device 80 may also receive data from a camera and from the input devices and sensors as mentioned previously. This data may be stored in a digital storage medium and may be further processed. For example, a set of images may be received and then calculated to determine a volume of a specimen 84. The computing device 80 may also send signals, such as images, to a screen 22 or other display device.

Next, a hardware description of the computing device 80 according to exemplary embodiments is described with reference to FIG. 6. Here, the computing device 80 includes a CPU 600 which performs the processes described above and below. The process data and instructions may be stored in memory 602. These processes and instructions may also be stored on a digital storage medium 604 such as a hard drive (HDD) or portable storage medium or may be stored remotely. Further, the claimed advancements are not limited by the form of the computer-readable medium on which the instructions of the inventive process are stored. For example, the instructions may be stored on CDs, DVDs, in FLASH memory, RAM, ROM, PROM, EPROM, EEPROM, hard disk, solid-state drive, and/or any other information processing device with which the computing device 80 communicates, such as a server, computer, or camera. In one embodiment, the digital storage medium 604 comprises a memory card that can be removed and exchanged. The digital storage medium 604 of the computing device may have a formatted capacity of 100 MB-10 TB, preferably 500 MB-1 TB, more preferably 1 GB-600 GB.

Further, the claimed advancements may be provided as a utility application, background daemon, or component of an operating system, or combination thereof, executing in conjunction with CPU 600 and an operating system such as Microsoft Windows 7, UNIX, Solaris, LINUX, Apple macOS, and other systems known to those skilled in the art.

The hardware elements of the computing device 80 may be realized by various circuitry elements, known to those skilled in the art. For example, CPU 600 may be a Xenon or Core processor from Intel of America or an Opteron processor from AMD of America, or may be other processor types that would be recognized by one of ordinary skill in the art. Alternatively, the CPU 600 may be implemented on an FPGA, ASIC, or PLD, or the CPU may use discrete logic circuits, as one of ordinary skill in the art would recognize. Further, the CPU 600 may be implemented as multiple processors cooperatively working in parallel to perform the instructions of the inventive processes described above and below.

Figure 6:
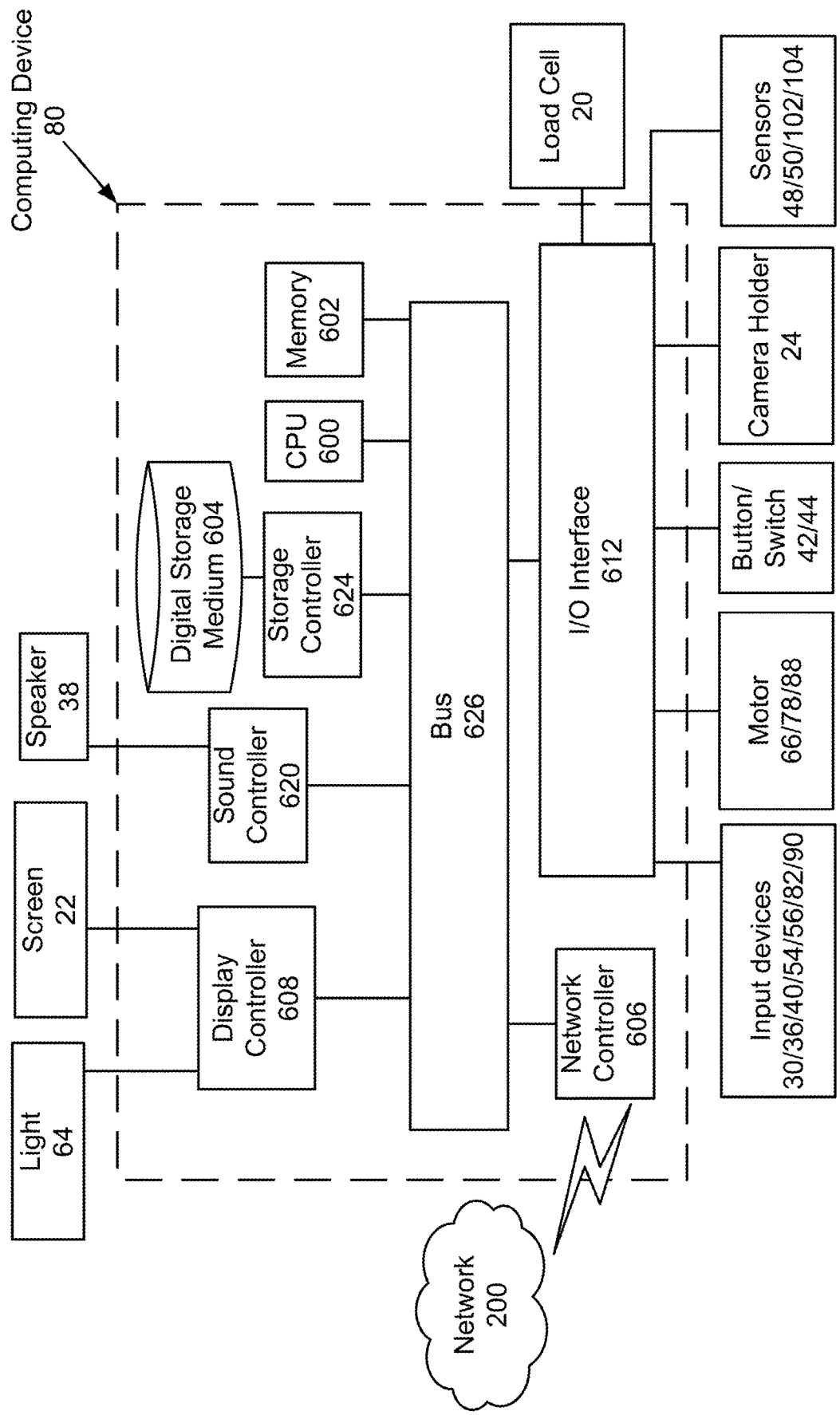
FIG. 6 is a diagram of the computing device and its connections.

The computing device 80 in FIG. 6 may also include a network controller 606, such as an Intel Ethernet PRO network interface card from Intel of America, for interfacing with a network 200. As can be appreciated, the network 200 may be a public network, such as the Internet, or a private network such as an LAN or WAN network, or any combination thereof, and may also include PSTN or ISDN sub-networks. The network 200 can also be wired, such as an Ethernet network, or can be wireless such as a cellular network including EDGE, 3G, and 4G wireless cellular systems. The wireless network can also be WiFi, Bluetooth, ANT, DASH7, ISA100.11a, MiWi, near-field communication, OCARI, ONE-NET, TSMP, WirelessHART, ZigBee, Z-Wave, and/or any other known form of wireless communication.

The computing device 80, as shown in FIG. 6, may include a display controller 608, such as a NVIDIA GeForce GTX or Quadro graphics adaptor from NVIDIA Corporation of America. The display controller 608 may interface with the screen 22, or an attached monitor or projector. The display controller 608 may also interface with indicator lights on the housing 14. A general purpose I/O interface 612 may connect with previously mentioned devices and sensors, such as a load cell 20, button panel 56, keyboard 82, touchscreen 30, microphone 36, IR camera 40, electrode 48, ultrasound transducer 50, barcode scanner 54, RFID chip/tag reader 90, spectrometer 102, thermometer 104, camera holder 24, buttons and switches 42/44 and motors 66/78/88.

A sound controller 620 may be provided in the computing device 80, such as Sound Blaster X-Fi Titanium from Creative, to interface a speaker 38 to provide alerting sounds or melodies, or to play back recorded observations associated with a particular case.

A general purpose storage controller 624 may connect to a digital storage medium 604 with communication bus 626, which may be an ISA, EISA, VESA, PCI, or similar communication bus, for interconnecting all of the components of the computing device 80.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset.

According to a second aspect, the present disclosure relates to a method of measuring a specimen 84 with the grossing workstation 10 of the first aspect. The method involves placing a specimen 84 on the balance pan 18, and pushing the screen 22 or a button 28/42 on the camera holder 24 or housing 14 to trigger the computing device 80 to receive a first image from a digital camera secured to the camera holder 24 and store the first image with a weight measurement of the specimen. This embodiment enables one-button operation for specimen examination and record-keeping. Pushing the screen 22 may involve pushing or touching an image of a button on a touch-sensitive screen 30. Other embodiments may enable hands-free triggering such as by triggering a foot switch, making a hand gesture in front of an IR camera 40, or triggering the RFID tag reader 90 with a tag in the specimen 84. In another embodiment, the triggering may simply be a result of the load cell 20 or other sensor detecting a specimen 84 on the balance pan 18. In another embodiment, the triggering may occur by pushing a button on a camera in the camera holder 24.

In one embodiment, the first image captures at least a part of a calibration marking on the balance pan 18. This calibration marking, such as a scale or graduated marking as mentioned previously, may allow a user to manually calculate the scale of the image, though in another embodiment, the computing device 80 may be able to identify the calibration markings in an image and automatically set the scale. For instance, with an above view or side view image, the computing device 80 may calculate that 100 pixels scales to 1 cm. In another embodiment, the calibration markings may enable the computing device 80 to determine the perspective angle of the camera, and adjust the scale accordingly in different regions of a picture. For instance, in a bottom corner of an image, the scale may be 500 pixels to 1 cm, while in an upper corner of the image, which may capture light further from the camera, 10 pixels may be equivalent to 1 cm. This image measurement may be considered a type of photogrammetry.

In one embodiment, the method further comprises the step of rotating the specimen 84 or moving the camera holder 24. The computing device 80 receives and stores at least one second image after the rotating or moving. Rotating the specimen involves rotating the balance pan 18, which may be done manually or automatically, and moving the camera holder 24 may be done manually or automatically. In one embodiment, between capturing a first image and a second image, the balance pan 18 is rotated and the camera holder 24 is moved. In an alternative embodiment, instead of rotating the balance pan 18, a user may manually rotate or flip a specimen 84 in relation to the balance pan 18. In one embodiment, where the moving of the balance pan and/or camera holder is done manually, the computing device may track the movement and alert a user with a noise or image when to stop at a particular position. For example, the speaker may emit a beep for every 30° that a rotatable balance pan is manually turned, so that a user may stop and take an image at those regular intervals.

In one embodiment, a user may manually trigger the camera to record a second image, however, in another embodiment, a user may only trigger the first image, with the above movements by a motor and second image capture occurring automatically. In one embodiment, the balance pan 18 may be turned 178-182°, or about 180° between the first and second images. In another embodiment, the balance pan 18 may be turned 88-92°, or about 90° between the first and second images. In one embodiment, the camera holder 24 may be moved an angle of 88-92°, or about 90° from the first image, where the vertex of the angle is in a central portion of the balance pan 18. Alternatively, the camera holder 24 and/or balance pan 18 may be moved by an angle of 35-65°, preferably 40-50°, more preferably 42-48° between first and second images, or may be moved by an angle of 1-40°, preferably 5-30°, more preferably 10-20°. The time between a first image and a second image may be 0.25-60 s, preferably 0.5-30 s, more preferably 0.75-10 s.

A single specimen 84 may have more than two images taken. For example, in one embodiment, five images may be taken each at five different views, which may be the top view of a specimen and four side views (front, back, left, right). Here, the five views are separated by substantially perpendicular angles. In another embodiment, several more images may be taken at different view angles and perspectives, at regular or irregular view angles.

In another embodiment, a camera holder 24 may move without aiming a camera at a particular position; for instance, the camera holder 24 in FIG. 4 may position a camera view angle parallel to the top side 16 of the balance pan, and may translate a camera up and/or down while maintaining a view parallel with the top side 16. In this embodiment, the camera holder 24 may move 0.3-3 cm, preferably 0.4-2.5 cm, more preferably 0.5-2 cm between images.

In one embodiment, a camera may take images from a stationary camera holder 24 while the balance pan 18 rotates. In another embodiment, a camera may take images of a specimen 84 on a stationary balance pan 18 while the camera holder 24 moves. In a preferred embodiment, a single imaging routine of a single specimen 84 may comprise 5-500, preferably 10-100, more preferably 12-80 images from unique view angles. This single imaging routine may be taken over a time span of 15 s-10 min, preferably 20 s-5 min, more preferably 30 s-4 min. Preferably between each image capture, a camera in the camera holder 24 is able to readjust the imaging settings, such as the focus. Alternatively, a series of image frames or a movie may be taken by a camera having a video mode. Preferably, where a workstation may take several sequential images as part of an imaging routine, preferably the housing has a button or switch to cancel or stop an imaging routine. FIG. 2 shows a workstation 10 with a cancel button 44 on the top side 16 of the housing. Instead of, or in addition to, a cancel button 44 on the housing, a workstation may have a cancel button on the camera holder 24, within the button panel 56, or may be an image of a button on a touch-sensitive screen 30.

In a further embodiment, the method further comprises the step of calculating a bulk density of the specimen 84 from the first image, the at least one second image, and the weight measurement. In this embodiment, the angle between the specimen viewpoints may be substantially perpendicular, for example 85-95°, preferably 87-93°, or about 90°. Preferably the two images are able to capture an approximate length, width, and height of a specimen 84 on the balance pan 18. The computing device 80 may be able to interpret these measurements based on the calibration scale, and use these measurements to calculate a volume. Then, with a weight measurement from the load cell 20, the computing device 80 is able to calculate the bulk density of the specimen 84. Preferably the bulk density and any other calculated properties are displayed on the screen 22 and/or stored in a digital file.

In one embodiment, the grossing workstation 10 may use two or more images from one or more camera view angles to construct a 3D image. Preferably this may be with 5-500, preferably 10-100, more preferably 12-80 images from unique view angles. This may use a process of stereophotogrammetry, which involves calculating the 3D coordinates of points on a specimen 84 using measurements made in two or more images taken from different positions. In this embodiment, the workstation may function similarly to a 3D scanner, and may be able to export a 3D image or structure file, such as an STL file, an AMF file, a PLY file, a Wavefront.obj file, an X3D file, or some other CAD or 3D file to a separate viewer or a 3D printer. Preferably, the color and/or texture of the specimen is visible in a 3D image. In one embodiment, a 3D image may be constructed and viewed on a screen 22 of the workstation or with an attached monitor or viewer, and a 3D image may be saved with a particular case file or converted to a different file format, such as a JPEG image file of a constructed perspective view or an AVI movie file of a rotating specimen. In one embodiment, where the electronic scale 12 has sensors measuring properties of a specimen, these properties may be combined with an image, including a constructed 3D image. For instance, an ultrasonography image may be mapped into a 3D wireframe model of a specimen. As another example, temperature or electrical conductivity data may be color-coded onto a 3D model of a specimen. In another embodiment, where a specimen 84 is imaged on a rack 76, the structure of the rack may be subtracted from or not incorporated within a constructed 3D model.

In alternative embodiments, the grossing workstation 10 may be used in areas outside of forensics, pathology, and autopsy. The grossing workstation may be used with specimens from scientific disciplines such as archeology, botany, entomology, geology, biology, and chemistry. The workstation may also be used in various arts, such as sculpture, computer graphics, architecture, culinary arts, and industrial design.

The invention claimed is:

1. A grossing workstation, comprising:
   an electronic scale having a housing with a top side;
   a computing device disposed within the housing and electrically connected to a load cell;
   a circular balance pan located on the top side of the housing, the balance pan disposed on the load cell, wherein the balance pan has a specimen side and an opposing bottom side, the specimen side configured to contact a specimen and the balance pan has a raised edge from the specimen side to contain liquids;
   wherein the balance pan is rotatable around a central axis perpendicular to the specimen side by frictional coupling to a disc rotatably connected to a pedestal motor inside the housing, wherein an outer surface of the disc has an elastomeric material in pressed contact with the circumference of the balance pan and the pedestal motor is electrically connected to the computing device and configured to rotate the disc;
   a screen attached to the housing and electrically connected to the computing device; and
   a camera holder attached to the housing by an arm, and electrically connected to the computing device, wherein the arm projects upwardly from the top side of the housing and curves inwardly toward the balance pan from a point of attachment to the top side of the housing from an edge of the top side of the housing;
   wherein the arm includes a motor and an actuator to move the camera holder along the arm, the motor electrically connected to the computing device and configured to control the position of the camera holder on the arm via the actuator;
   wherein the camera holder is configured to secure and electrically connect with a digital camera to image the specimen on the balance pan,
   wherein the specimen side comprises an electrode electrically connected to the computing device and configured to measure a conductance or a capacitance of the specimen,
   wherein the specimen side further comprises an ultrasonic transducer, a spectrometer, and a thermometer, and
   wherein the ultrasonic transducer is in direct contact with the specimen side of the balance pan.

2. The grossing workstation of claim 1, further comprising at least one input device electrically connected to the computing device,
   wherein the at least one input device is a microphone.

3. The grossing workstation of claim 2, further comprising at least one second input device,
   wherein the at least one second input device is at least one selected from the group consisting of a barcode scanner, an infrared camera, and an RFID tag reader.

4. The grossing workstation of claim 2, further comprising at least one second input device,
   wherein the at least one second input device is a keyboard, a touchscreen, or a button panel, and wherein the at least one second input device is slidably attached to one or more rails and configured to slide between a first position within an interior of the housing and a second position extending from a first side of the housing.

5. The grossing workstation of claim 4, wherein the screen is attached to a second side of the housing opposing the first side.

6. The grossing workstation of claim 5, wherein the screen is attached to the second side of the housing by a hinge or an adjustable mount.

7. The grossing workstation of claim 1, wherein the actuator is at least one selected from the group consisting of a lead screw, a belt drive, a worm drive, a rack and pinion drive, and a chain drive.

8. The grossing workstation of claim 1, wherein the balance pan has one or more graduated markings configured to measure one or more dimensions of a specimen.

9. The grossing workstation of claim 1, wherein the balance pan comprises a rack, the rack being configured to elevate the specimen.

10. The grossing workstation of claim 1, further comprising a second arm attached to the housing, and the second arm having one or more lights configured to illuminate the specimen.

11. The grossing workstation of claim 3, wherein the at least one second input device is an infrared camera.

12. A grossing workstation, comprising:
    an electronic scale having a housing with a top side;
    a computing device disposed within the housing and electrically connected to a load cell;
    a circular balance pan located on the top side of the housing, the balance pan disposed on the load cell, wherein the balance pan has a top specimen side and an opposing bottom side, the specimen side configured to contact a specimen and the balance pan has a raised edge from the specimen side to contain liquids;
    wherein the balance pan is rotatable around a central axis perpendicular to the specimen side by frictional coupling to a disc rotatably connected to a pedestal motor inside the housing, wherein an outer surface of the disc has an elastomeric material in pressed contact with the circumference of the balance pan and the pedestal motor is electrically connected to the computing device and configured to rotate the disc;

a screen attached to the housing and electrically connected to the computing device; and a camera holder attached to the housing by an arm, and electrically connected to the computing device, wherein the arm arches over the balance pan across the axis of the balance pan from a first connection point on the top side of the housing to a second connection point on the top side of the housing, wherein the first and second connection points are on opposing sides of the balance pan proximal to respective edges of the housing;

wherein the arm includes a motor and an actuator to move the camera holder along the arm, the motor electrically connected to the computing device and configured to control the position of the camera holder on the arm via the actuator;

wherein the camera holder is configured to secure and electrically connect with a digital camera to image the specimen on the balance pan, wherein the specimen side comprises an electrode electrically connected to the computing device and configured to measure a conductance or a capacitance of the specimen, wherein the specimen side further comprises an ultrasonic transducer, a spectrometer, and a thermometer, and wherein the ultrasonic transducer is in direct contact with the specimen side of the balance pan.

\* \* \* \* \*